United States Patent [19]

Aldridge, Jr. et al.

[11] 4,207,394
[45] * Jun. 10, 1980

[54] PROCESS AND APPARATUS FOR ANALYZING SPECIMENS FOR THE PRESENCE OF MICROORGANISMS THEREIN

[75] Inventors: Clifton Aldridge, Jr., Creve Coeur; Paul W. Jones, St. Charles; Sandra F. Gibson, St. Ann; Richard D. Vannest, St. Charles; James T. Holen, Florissant; George F. Keyser, St. Louis, all of Mo.; Michael C. Meyer, Belleville, Ill.

[73] Assignee: McDonnell Douglas Corporation, St. Louis, Mo.

[*] Notice: The portion of the term of this patent subsequent to Jun. 15, 1993, has been disclaimed.

[21] Appl. No.: 854,592

[22] Filed: Nov. 25, 1977

Related U.S. Application Data

[60] Continuation of Ser. No. 652,991, Jan. 28, 1976, abandoned, which is a division of Ser. No. 461,249, Apr. 16, 1974, Pat. No. 3,963,355, which is a continuation of Ser. No. 255,533, May 22, 1972, abandoned.

[51] Int. Cl.² .......................... C12Q 1/04; C12M 1/18
[52] U.S. Cl. ........................................ 435/34; 422/61; 435/300; 435/301; 435/287; 435/291
[58] Field of Search ................. 195/103.5 M, 127, 139, 195/140; 422/61; 356/246

[56] References Cited

U.S. PATENT DOCUMENTS

| | | | |
|---|---|---|---|
| 3,691,017 | 9/1972 | Brown et al. | 422/61 X |
| 3,799,742 | 3/1974 | Coleman | 422/61 |
| 3,922,203 | 11/1975 | Aldridge, Jr. et al. | 195/103.5 M |
| 3,963,355 | 6/1976 | Aldridge, Jr. et al. | 195/127 X |

OTHER PUBLICATIONS

Robert Bailey and Edwyn Scott, Diagnostic Microbiology; 2nd Edition, The C.V. Mosby Company; pp. 295 and 296; 1966.

Martin Frobisher, Fundamentals of Microbiology, 8th Edition, W. B. Saunders Company, p. 47; 1968.

*Primary Examiner*—Alvin E. Tanenholtz
*Assistant Examiner*—Robert J. Warden
*Attorney, Agent, or Firm*—Gravely, Lieder & Woodruff

[57] ABSTRACT

Microorganisms in a specimen are detected, identified, and enumerated by introducing the specimen into a sampling cartridge and diluting the specimen with a known volume of water within the cartridge. The cartridge has a manifold and several cassettes attached to the manifold. Each cassette contains a serpentine flow channel having a series of filters therein and a detection cell located downstream from each filter. The flow channel in each cassette also contains a culture medium which is freeze dried and is highly selective in the sense that it promotes the growth of one type of microorganism, but not others. The mixture of the specimen and water flows from the manifold into the flow channel of each cassette where it rehydrates the culture medium therein and further flows through the filters. Each filter removes a known proportion of the microorganisms from the mixture of specimen, water and medium, thereby effecting a serial dilution. After the cassettes are heated to incubate the microorganisms, the detection cells are observed for growth of the microorganisms therein which is manifested in a change in the light transmitting characteristics of the mixtures within the cells.

8 Claims, 13 Drawing Figures

4,207,394

PROCESS AND APPARATUS FOR ANALYZING SPECIMENS FOR THE PRESENCE OF MICROORGANISMS THEREIN

The invention described herein was made in the performance of work under a NASA contract and is subject to the provisions of the National Aeronautics and Space Act of 1958, Public Law 85-568 (75 Stat. 426; 42 U.S.C. 2451), as amended.

This is a continuation of application Ser. No. 652,991 now abandoned, filed Jan. 28, 1976, which is a division of application Ser. No. 461,249, filed Apr. 16, 1974, now U.S. Pat. No. 3,963,355, which is a continuation of abandoned application Ser. No. 255,533, filed May 22, 1972.

BACKGROUND OF THE INVENTION

This invention relates to a process and apparatus for analyzing specimens for the presence of microorganisms therein, and more particularly to a process and apparatus for detecting, identifying and enumerating microorganisms in specimens.

The detection and identification of microorganisms is an important aspect of many medically-related sciences, but heretofore has been a difficult and time-consuming procedure, requiring highly skilled personnel. In particular, the conventional procedure for detecting and identifying microorganisms involves collecting a specimen on a swab and then wiping the swab over a nutrient surface which is compatible with the microorganisms to which the analysis is directed. After incubating the culture medium for 24 to 48 hours, the culture is examined for pure colonies. In some instances the pure colonies can be identified merely by microscopic examination, but many times the appearance of a colony provides only a suggestion as to the specific organism. In any event, the pure colony must be isolated and incubated still further so that biochemical tests may be conducted to verify the identification.

In order to obtain a count of the microorganisms, the specimen is placed on a nutrient surface which is highly selective in that it will make one species stand out and be clearly discernible from others by color or some other indication. After incubation, the microorganisms of the selected species grow into colonies which are readily recognized and may be counted. In many instances, the initial incubation produces a large biomass. Hence, the specimen must be serial diluted and each dilution incubated and examined until one containing distinct colonies is obtained. These colonies are then counted and the total number is ascertained by multiplying the count by the dilution factor. Again, long time intervals are required for incubation, and the count therefore requires considerable time. A typical interval between sampling and identification may be 2 to 3 days. This lost time often is critical to a seriously ill patient.

The foregoing procedures are employed for detecting, identifying, and counting many common bacterial and fungal organisms such as:

Staphylococcus aureus (coagulas positive)
Salmonella species (including typhosa)
Pseudomonas aeruginaso
Proteus species
Coliform organisms including Escherichia coli
Herella species
Streptococcus pyrogenes (Type A)
Candida albicans It is impossible to analyze specimens from space travelers to diagnose their illness with any degree of accuracy. This invention allows the taking and incubation of specimens in space craft. Transmitting the results to earth for analysis, diagnosis and prescribing of treatment.

SUMMARY OF THE INVENTION

One of the principal objects of the present invention is to provide a process and apparatus for easily and quickly detecting, identifying, and enumerating medically important microorganisms. Another object is to provide a process and apparatus of the type stated which does not require highly skilled personnel. A further object is to provide a process and apparatus which is ideally suited for analyzing human clinical specimens from the throat, skin, feces and urine for the presence of medically impotant microorganisms. An additional object is to provide culture media which are highly selective and undergo a change which is optically perceptible upon the growth of microorganisms therein. Still another object is to provide media of the type stated which have a long shelf life. Yet another object is to provide a process and apparatus of the type stated which produces unique time-related signature characteristics for certain microorganisms. A further object is to provide an apparatus in which the microorganisms are completely contained so little hazard exists of having them escape. These and other objects and advantages will become apparent hereinafter.

The present invention is embodied in a process for detecting and identifying microorganisms in a specimen, and that process involves diluting the specimen in a liquid, mixing the mixture so formed with a highly selective culture medium to form another mixture, and observing the relative optical density of the last mixture. The invention also resides in the individual culture media and in the analytical apparatus for performing the foregoing process. The invention also consists in the parts and in the arrangements and combinations of parts hereinafter described and claimed.

DESCRIPTION OF THE DRAWINGS

In the accompanying drawings which form part of the specification and wherein like numerals refer to like parts wherever they occur.

DETAILED DESCRIPTION

Figure 1:
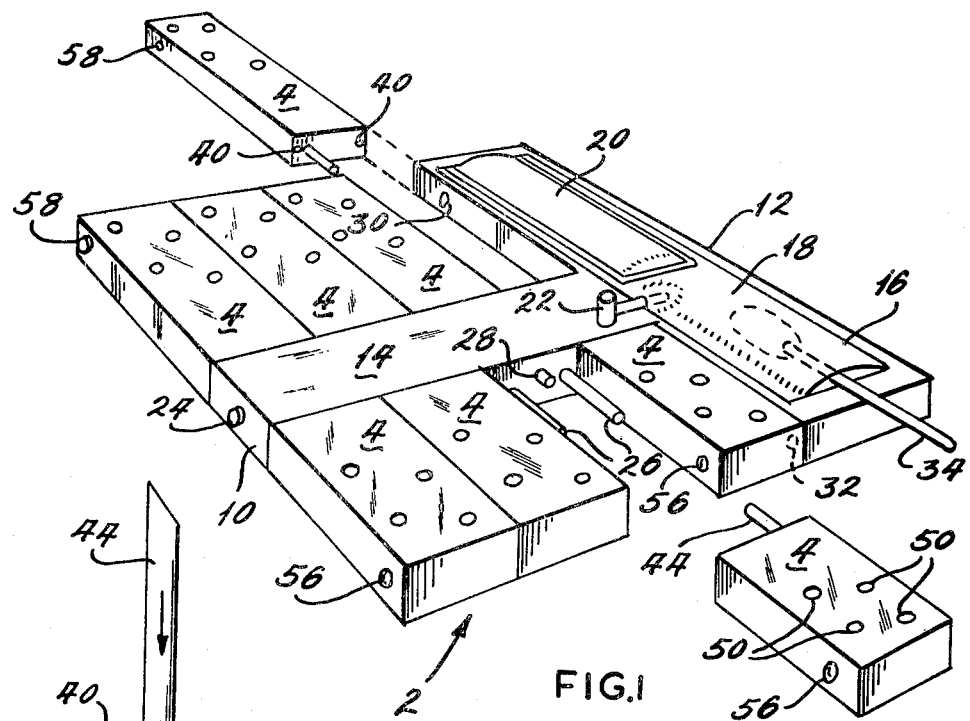
FIG. 1 is a perspective view of a microbial sampling cartridge forming part of the present invention.

Referring now to the drawings, an analytical apparatus, called a microbial load monitor is utilized to detect, identify and enumerate medically important microorganisms. That apparatus basically includes a microbial sampling cartridge 2 into which a specimen suspected of containing certain microorganisms is introduced, and this cartridge has a plurality of detachable cassettes, 4, each of which undergoes an optically perceptible change when a selected microorganism grows in it. In addition, the apparatus includes an electro-optical detector 6 which incubates the microorganism in the cassettes 4 after the cassettes 4 are detached from the body of the cartridge 2 and detects and records changes in the light transmitting characteristics thereof.

THE MICROBIAL SAMPLING CARTRIDGE

The sampling cartridge 2 comprises (FIG. 1) a generally T-shaped from 10 composed of an end portion 12 and a manifold 14 joined to the end portion 12 and projecting from the center thereof. The end portion 12 has an upwardly opening cavity 16 which extends substantially the entire length thereof, and this cavity 16 contains a plastic outer bag 18 which is closed along its two side margins and also along one of its end margins. The other end of the plastic bag 18 is left open to provide access to the bag interior. Disposed within the outer bag 18 is a diluent reservoir 20, which is actually another bag completely sealed and filled with a known volume of diluent conducive to the growth of microorganisms. Distilled water is ideally suited for this purpose.

The manifold 14 has a hollow interior which communicates with the interior of the outer bag 18 through a valve 22 located in the T-shaped frame 10 at the juncture of the manifold 14 and end portion 12, and thus forms a flow channel leading from the bag 18. At its opposite end the manifold 14 has a septum 24 which normally seals the end of the manifold 14, but affords access to the interior of the manifold 14 when punctured with a sharp implement such as a hollow needle. Of course, when the puncturing implement is withdrawn the septum 24 reseals itself. Along each of its sides, the manifiold 14 is provided with guide pins 26 arranged in pairs and between the guide pins 26 of each pair, the manifold 14 is further provided with septa 28. The septa 28 likewise afford access to the interior of the manifold 14 when punctured.

On one side of the manifold 14, the side of the end portion 12 has a locking detent 30 and on the other side it has a locking indent 32.

The sampling cartridge 2 receives a swab 34, the tip of which carries the specimen sample which is to be analyzed. In particular, the swab 34 is inserted into the open end of the bag 18 and then its handle is broken off, leaving only the swab tip and the specimen in the bag 18. Next, the detached end margins of the plastic bag are heat sealed together so that the specimen is completely sealed within the bag 18.

Figure 2:
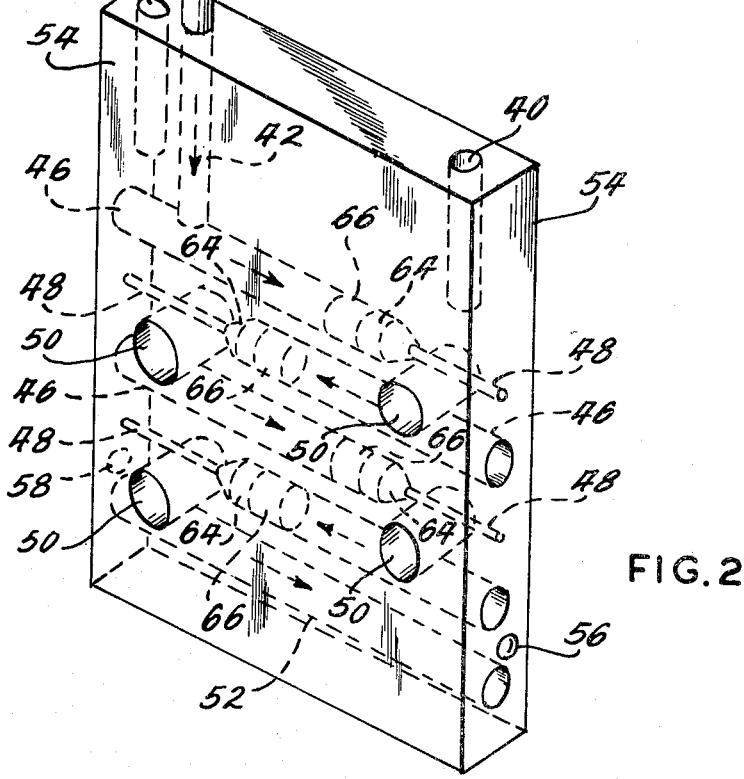
FIG. 2 is a perspective view of a cassette which forms part of the sampling cartridge.

The cassettes 4 (FIG. 2) are part of the sampling cartridge 2 and are formed from a clear plastic such as polycarbonate or a high density polyethylene. They are rectangular in shape and resemble small chips. Indeed, cassettes 4 measuring 1"×¾"×⅛" have been found to be ideally suited for the present invention.

Each cassette 4 has a pair of guide holes 40 opening out of one end thereof, and these guide holes are sized and spaced such that they receive the guide pins 26 of any pair projecting from the manifold 14 of the T-shaped frame 10. Each cassette 4 is further provided with an inlet port 42 which extends longitudinally therein and opens outwardly next to one of the guide holes 40. The inlet port 42 contains a hollow innoculating needle 44 which projects outwardly therefrom and aligns with the septum 28 between a pair of guide pins 26 when those guide pins 26 align with the guide holes 40. Thus, as the cassette 4 is pressed toward the manifold 14 with the guide pins 26 in the guide holes 40, the hollow innoclating needle 44 will puncture the septum 28 disposed in its path and provide communication between interior of the manifold 14 and the inlet port 42.

In addition to the inlet port 42, the cassette 4 is provided with for transfer bores 46 which are parallel to one another and perpendicular to the inlet port 42. Thus, the transfer bores 46 extend transversely across the cassette 4. The upstream end of each transfer bore 46 opens outwardly through the sides of the cassette 4, and these ends are plugged with a suitable sealing composition. The downstream end of each transfer bore 46 is reduced considerably, forming a reduced terminal end 48 which is also plugged. The inlet port 42 opens into the upstream end of the first transfer bore 46, while the reduced terminal end 50 of that first bore opens into the side of a detection cell 50. The opposite side of that detection cell 50 opens into the upstream end of the second transfer bore 46. Similarly, the downstream end of the second transfer bore 46 and the upstream end of the third bore 46 are connected by another detection cell 50 and so are the downstream end third bore 46 and the upstream end of the fourth bore 46. Thus, the transfer bores 46 in conjunction with the connecting detection cells 50 form a serpentine flow channel through the cassette 4. The detection cells 50 are actually bores extending completely through the cassette 4 and oriented such that their axes are parallel to one another and perpendicular to the plane in which the axes for the transfer bores 46 lie. Instead of opening into the upstream end of another transfer bore 46, the side of the fourth detection cell 50 opens into an overflow reservoir 52 which is another bore plugged at its ends and extending parallel to the transfer bores 46. The ends of the detection cells 50 are covered and sealed by transparent tape strips 54 which adhere to the top and bottom surfaces of the cassette 4.

Each cassette 4 further has a locking intent 56 on one of its side faces and a locking detent 58 on its opposite face, and the intents 56 and detents 58 of adjacent cassettes 4 engage one another when supported in the proper position on the manifold 14. Moreover, the indent 58 of the innermost cassette 4 on one side of the manifold 14 engages the detent 30 on the end portion 2, while the detent 58 of the cassette 4 on the opposite side of the manifold 14 engages the indent 32 of the end portion 12.

Prior to the plugging of the ends of the transfer bores 46, those bores are fitted with small circular filters 58 positioned immediately ahead of the reduced terminal ends 48. Filters 58 composed of asbestos fibers are preferred, and the pore size and filter length should be such that 90% of the selected microorganisms for the cassette are removed at each filter 58. Thus, each filter 64 will account for a one log reduction. It has been found that the same filter size and filter length will account for a 90% reduction in all microorganisms passing through it, irrespective of whether they are bacterial or fungal organisms. Consequently, the filters 64 for all of the cassettes are the same, notwithstanding the fact that the various cassettes 4 are selective as to different microorganisms.

The filter material used in the cassette filtration system consists of approximately 0.001 g. asbestos fibers in each transfer bore 46. The fibers were obtained from a Seitz asbestos fiber pad. It is published in a scientific products catalog that an approximate 3 mm filter pad has a pore size in the 2 micron range. It is thought that dilution of organisms occurs by absorption rather than filtration. Hence, pore size is insignificant.

In addition to a filter 64, each transfer bore 46 further contains a bed or packing 66 of culture medium, and that bed is positioned upstream therein from the filter 64. The culture medium is preferably freeze dried and each bed 66 thereof is rehydrated upon the passage of water through the transfer bore 46 in which it is disposed. The culture medium is highly selective with regard to the microorganisms in the sense that it undergoes a perceptible change from an optical standpoint only when one type of microorganism, that is the favored microorganism, grows in it. Thus, an optical change is detected at the four detection cells 50 in the cassette 4, and usually becomes progressively greater with the passage of time, provided of course that the selected microorganism grows in the cassette 4. The change may be observed with the naked eye or by the electro-optical detector 6.

Thus, the culture medium for each cassette 4 is different, and the exact compositions of the culture medium for various microorganisms will be discussed hereinafter. Finally, it shold be noted that most of the culture medium for each cassette 4 is concentrated ahead of the first filter 64, for otherwise the culture medium when it goes into solution would reach its greatest concentration in the fourth or last detection cell 50. With respect to most of the culture media developed, it has been determined empirically that 50% by weight of the medium for the cassette 4 should be in the first transfer bore 46, 25% in the second bore 46, and 12.5% in each of the third and fourth bores 46. When so proportioned, the concentrations of the culture medium are about the same in each detection cell 50 upon the subsequent hydration of the culture medium as the water passes through it.

Each cassette 4 should be labeled with the name of or at least some code designating the microorganism for which the culture medium therein is selective.

THE SELECTIVE MEDIA

Each cassette 4 contains a different selective medium, and each medium favors one species of microorganisms in the sense that the favored microorganism will grow in the medium in a specific pattern and thereby change its light transmitting characteristics. The change is usually the result of a precipitate forming or a change in color. In any event, the change increases the relative optical density of the solution and may be observed in the detection cells 50. The change is readily detected in light of 665 nanometers wave length. Moreover, all of the media may be freeze dried and when so dried has a storage life of at least 6 months. In addition, the media is sensitive enough to promote growth where the bacterial or fungal populations are as small as 1000 microorganisms per milliliter.

The following media are suitable for detecting the microorganisms so indicated.

1. STAPHYLOCOCCUS MEDIUM

*Staphylococcus aureus* causes abscesses, pustules, and fatal septicemias and will grow in a medium which is prepared by first mixing the following ingredients in 930 ml. of distilled water:

Beef Extract: 1 g.
Polypeptone peptone: 10 g.
NaCl: 75 g.
D-mannitol: 10 g.
K$_2$HPO$_4$: 1 g.

Thereafter, the medium is sterilized in an autoclave for 15 minutes at 15 psi. After the medium cools, 1 ml. of 1% KTe (potassium tellurite) and 70 g. of sterile fresh egg yoke (chicken) are added. Then the pH is adjusted with sterile phosphates (1/15M) to 7.2. Finally, the medium is dehydrated by freeze drying.

In the cassette 4 for the staphylococcus medium the bed 66 in the first transfer bore 46 should contain 50% by weight of the total amount of medium for the cassette 4, whereas the second culture bed 66 should contain 25%. The third and fourth culture beds should contain 12.5% each.

The critical ingredients are potassium tellurite and egg yolk. The ingredient may vary (in weight percent based on the weight of dry ingredients) from 0.3 to 2.0% beef extract; from 8.0 to 12.0% polypeptone peptone; from 75.0 to 80.0% NaCl; from 5.4 to 14.5% D-mannitol; from 0.8 to 1.2% K$_2$HOP$_4$; from 0.0005 to 0.0015% potassium tellurite; and from 0.7 to 1.3% egg yolks.

The pH of the solution should be between 6.5 to 8.0.

2. UREASE (PROTEUS) MEDIUM

The proteus species is usually found in the intestine and causes bladder and intestinal infections, occasionally infects burned tissue. It is favored by a medium which is prepared by mixing the following ingredients with 1.0 liter of distilled water:

Glucose: 1 g.
Gelysate: 2 g.
Urea: 30 g.
KH$_2$PO$_4$: 1.4 g.
K$_2$HPO$_4$: 1.0 g.
NaCl: 5 g.
MgSO$_4$: 10 g.

Thereafter, the pH is adjusted to 6.8 with phosphates and the mixture is filtered to sterilize. Finally, the sterilized mixture is dehydrated by freeze drying.

The medium should be distributed with 50%, 25%, 12.5% and 12.5% by weight in the first, second, third, and fourth culture beds 66, respectively.

The ingredients may vary (in weight percent based on the weight of dry ingredients) from 1.0 to 3.0% glucose; from 3.0 to 5.0% gelysate; from 4.2 to 13.4% NaCl; from 2.4 to 3.2% KH$_2$PO$_4$; from 1.8 to 2.5% K$_2$HPO$_4$; from 55.0 to 63.0% urea; and from 16.0 to 23.0% MgSO$_4$.

The pH of the solution should be between 6.0 to 7.2.

Gelysate is a bacteriological peptone, pancreatic hydrolysate of gelatin.

3. CANDIDA BROTH

The Candida species is found primarily in specimens derived from skin and throat specimens and causes thrush. It grows in a selective medium prepared as follows. Into 1.0 liter of water the following ingredients are introduced:

Phytone peptone: 10 g.
Dextrose: 10 g.
Cyclohexamide: 0.4 g.
Chloramphenicol: 0.05 g.

The above ingredients are heated slightly to dissolve, the pH is adjusted with phosphate to 6.9, and the ingredients are filter sterilized. Next, 25 mg/l of colymycin and 25 mg/l of naladixic acid are added.

The medium should be distributed with 50%, 25%, 12.5% and 12.5% in the first, second, third and fourth culture beds, respectively.

The ingredients may very (in weight percent based on the weight of dry ingredients) from 45 to 50% phytone peptone; from 45 to 50% dextrose; from 2.0% to 3.0% cyclohexamide; from 0.2 to 3.0% chloramphenicol; from 0.1 to 0.15% colymycin; from 0.1 to 0.15 nalidixic acid.

The pH of the solution should be between 6 to 7.8.

Phytone is a papaic digest of soya meal (bacteriological peptone). Colymycin is sodium colistimatate (D.Bucaine). Nalidixic acid is negram and is sold by the Winthrop Company.

4. PSEUDOMONAS AERUGINOSA BROTH

Pseudomonas aeruginosa is found primarily in water samples. Clinically it may be found in urine, wound and fecal specimens, but is basically non-pathogenic. The medium which favors it is formed by introducing the following ingredients into 1.0 liter of distilled water:

Bio Chart Tryptic Soy Broth: 30 g.

Cetrimide (Cetyl trimethylammonium bromide): 2 g. The mixture so formed is heated to dissolve the ingredients and thereater phosphates are added to adjust the pH to 7.5. The solution is filtered to sterilize it. Finally, the solution is dehydrated by freeze drying.

The foregoing medium is extremely soluble in water, and by reason of this fact a greater percentage of it must be contained in the first culture bed 66. Indeed, it has been determined empirically that 90% of the medium by weight should be in the first culture bed 66 with the other 10% spread equally through the remaining three culture beds 66.

From 99.2 to 99.4% Tryptic Soy Broth and from 0.6% to 0.8% cetrimide can be used and the pH may vary from 6.0 to 8.5.

Biocert tryptic soy broth has the following composition per liter:

Typtone: 17.0 g.
Soy peptone: 3.0 g.
NaCl: 5.0
$K_2HPO_4$: 2.5
Glucose: 2.5 Cetrimide is cetyl trimethylammonium bromide.

5. COLIFORM BROTH

Coliform organisms (Escherichia coli) are formed primarily in fecal specimens and cause enteric infection. The selective medium for this microorganism is prepared by dissolving 10g. of lactose and 10 g. of gelysate in 1.0 liter of distilled water. Next, HCl or NaOH are added to bring the pH to 7.4. Thereafter, 10 g. of sodium desoxycholate are added. The mixture may be heated to dissolve the ingredients, but should not be brought to a boil. Finally, the solution is sterilized by filtering and 13.3 mg. of brilliant green are added.

The medium is distributed through the four culture beds 66 on a 50%, ;b 25%, 12.5% and 12.5% basis.

From 20% to 42.9% lactose, from 20 to 42.9% gelysate, from 20 to 42.9% sodium desoxycholate, and from 0.04 to 0.06% brilliant green can be used and the pH may vary from 6.6 to 8.5. The percents are by weight based on the weight of dry ingredients.

6. SALMONELLA BROTH

Salmonella typhosa and related species are usually found in fecal specimens and causes enteric infections. Its selective culture medium is prepared by adding the following ingredients to 1.0 liter of distilled water.

Sodium Acid Selenite: 5 g.
L-lysine Monohydrochloride: 10 g.
Ammonium Chloride: 3 g.
Yeast extract: 1 g.
$KH_2PO_4$: 1.8 g.
Phenol Red: 0.03 g.

The ingredients should be brought into the solution without the aid of heat. Once the ingredients are in the solution of pH is adjusted to 6.7 with phosphate. Thereafter, the solution is sterilized by filtering and is freeze dried.

The medium is distributed through the four culture beds on a 50%, 25%, 12.5% and 12.5% basis.

The critical ingredient is sodium acid selenite. The ingredients may vary (in weight percent based on the weight of dry ingredients) from 22.1 to 27.5% sodium acid selenite; from 42.5 to 52.6% L-lysine monohychloride; from 3.9 to 7.0% yeast extract, from 12.3 to 16% ammonium chloride, from 0.14 to 0.18% phenol red; and from 7.7 to 10.8 $KH_2PO_4$.

The pH of the solution should be between 6 to 8.

7. STREPTOCOCCUS BROTH

Streptococcus pyogenes (type A) causes strep throat, scarlet fever, and endocarditis. The selective medium for it is prepared by adding the following ingredients to 1 liter of distilled water.

Simplastin (dried): 1.5 g.
Oxalated horse plasma (dried): 5.0 g.
Neomycin sulfate: 0.003 g.
Potassium tellurite: 0.01 g.

All dried ingredients must be protected from moisture while stored. The addition of water causes the formation of a fibrin clot which is dissolved by the streptococci. The neomycin sulfate and potassium tellurite prevent the growth of all other organisms capable of dissolving fibrin clots.

The medium is distributed through the four culture beds on a 50%, 25%, 12.5% and 12.5% basis.

The critical ingredients are plasma, neomycin sulfate, potassium tellurite and simplastin. The ingredients may vary (in weight percent based on the weight of dry ingredients) from 16.6 to 28.5% simplastin; from 72.6 to 82.2% oxilated plasma; and from 0.14 to 0.17% potassium tellurite. The neomycin sulfate should be about 0.03%.

The pH of the solution should be between 6.0 to 7.8.

Simplastin is thromboplastin extract and that is a constituent in fibrin formation—Factor V, Factor VIII, Factor X, Factor VII, Hageman, Factor IX PTA, Platelets, $Ca^{++}$. It is available from Warner-Chilcott Laboratories, Morris Plains, N.J.

8. HERELLEA BROTH

Herellea species is found in specimens derived from urine, sputum, and wound specimen and causes minor infection. The medium for it is prepared by adding the following ingredients to 1 liter of distilled water.

2 g.—2-desoxy-D-glucose
1 g.—myosate polypeptone
0.8 g.—yeast extract
5 g.—tris buffer (2-amino-2[hydroxymethyl]-1;3-propanediol)

After the ingredients are in solution, the medium is filter sterilized. Then 0.5 ml/L nystatin from a stock concentration of 50,000 units/ml., and 0.07 g/L 2-aminothiazoline are added. 35. mg/L furadantin is then added to the medium. The final pH will be 9.1.

The medium is distributed through the four culture beds on a 50%, 25%, 12.5%, and 12.5 basis.

The critical ingredients are 2-aminothiazoline and furadantin. The ingredients may vary (in weight percent based on the weight of dry ingredients) from 6.75% to 36.68% 2-desoxy-D-glucose; from 5.95% to 23.0% myosate polypeptone; from 2.4% to 15.6% yeast extract; from 33.9 to 67.2% tris buffer; from 1000 to 25,000 units nystatin; from 0.6 to 1.3% 2-aminothiazoline; from 0.11 to 0.56% furadantin. The pH of the solution should be between 8.8 and 9.5.

Myosate polypeptone is a bacteriological peptone, pancreatic hydrolysis of cardiac muscle.

Furadantin is:
(nitrofurantoin sodium)
1-[(5-nitrofurfurylidene) amino]
Hydantoin sodium salt

OPERATION OF THE SAMPLING CARTRIDGE

As previously noted, the specimen to be analyzed is collected on the swab 34, and that swab is thereafter inserted into the plastic bag 18 through the open end thereof. Thereupon, the swab handle is broken off, leaving the swab tip in the bag 18. Next, the detached margins at the bag opening are heat sealed together so that the specimen is completely sealed within the bag 18.

In addition to introduced the specimen into the sampling cartridge 2, the user determines to which microorganisms he desires to address his analysis and selects cassettes 4 which are selective as to those microorganisms. These cassettes 4 are installed on manifold 14 by aligning their guide holes 40 with the guide pins 26 and then pressing them toward the manifold 14. This, of course, causes the hollow needles 44 of the cassettes 4 to pass through the septa 28 in the manifold 14 which in turn places the interior of the manifold 14 in communication with the inlet ports 42 of the cassettes 4.

Once the specimen is sealed within the plastic bag 18 and the selected cassettes 4 are in place along the sides of the manifold 14, the valve 22 is opened and a hollow needle (not shown), which is connected to a vacuum pump, is inserted through the septum 24 at the end of the manifold 14. The vacuum pump evacuates air from the manifold 14 and plastic bag 18, as well as from the inlet port 42, the transfer bores 46, the detection cells 50, and the overflow reservoir 52 of each cassette 4. Thereafter, the hollow vacuum needle is withdrawn from the septum 24 and the valve 22 is closed. Next the bag forming the diluent reservoir 20 is burst by manually compressing it against the wall at the bottom of the cavity 16, and this causes the known volume of water to flow therefrom into the plastic bag 18. The sampling cartridge 2 is then agitated to thoroughly mix the specimen with the water in the bag 18. Thereafter, the valve 22 is opened and the water having the specimen mixed therewith flows into the interior of the manifold 14 and thence into the cassettes 4 through the hollow needles 44.

Within each cassette 4, the mixture of water and specimen initially flows into the first of the four transfer bores 46 where the water dissolves or rehydrates the dried culture medium of the first bed 66 therein. The solution so formed passes through the first filter 64 where any particulate matter from the specimen is removed. The first filter 64 also removes 90% of the microorganisms, and in particular 90% of the type for which the particular culture medium is selective, so that the concentration of microorganisms is reduced to 10% of the concentration in the manifold 14 by the time the solution enters the first detection cell 50. Thereafter, the solution dissolves the bed 66 of dried medium present in the second transfer bore 46, and also flows through the filter 64 therein. The second filter 64 removes another 90% of the microorganisms so that the concentration of microorganisms in the second detection cell 50 is 10% of that within the first cell 50 and 1% of that within the manifold 14. The solution thereafter flows through the third bed 66 of culture medium where it dissolves still more culture medium and through the third filter 64 where another 90% of the microorganisms are removed. Thus, the solution entering the third detection cell 50 has only 10% of the microorganisms of the solution of the second detection cell 50. The solution dissolves still more culture medium as it passes through the fourth bed 66 of culture medium, and another 90% of the selective microorganisms are removed as the solution passes through the fourth filter 64. Thereater, the solution flows into the fourth detection cell 50 and thence into the overflow reservoir 52.

By proportioning the culture medium 66 in the manner previously discussed, that is with the greatest quantity in the bed 66 of the first transfer bore 46, it is possible to have the strength of the culture solutions in the four detection cells 50 substantially the same by the time the overflow reservoir 52 is filled. Thus, the conditions for promoting growth of the microorganisms is likewise the same in each detection cell 50. Moreover, the 90% reduction in the number of the selected microorganism at each filter 64 amounts to a ten fold serial dilution. Consequently, if $10^4$ of the selected microorganism exits in a given volume of water within the manifold 14, $10^3$ will exist in the same quantity of water within the first detection cell 50, although the water in that detection cell 50 will have the culture medium 66 dissolved in it to promote the growth of the microorganisms. Continuing on with the example, the same volume of water in the second detection cell 50 will have $10^2$ of the selected microorganisms while the same volume of water in the third and fourth detection cells 50 will have 10 and 1 of the selective microorganisms, respectively.

Initially, the solution containing the dissolved culture medium 66 and the microorganisms is clear or transparent. However, when the cassette 4 is heated, the type of microorganism favored by the culture medium 66 will grow and will change the light transmitting characteristics of the solution. This change occurs as a color variation or else as a precipitate formation, depending on the culture medium and microorganism, and the change is visually perceptible at the four detection cells 50. Since the first detection cell 50 contains the greatest concentration of the favored microorganism in most instances, it will transmit less light than the remaining cells 50. No change in the light transmitting characteristics of a cell 50 indicates the absence of the microorganism favored by the culture media or perhaps an insignificant number of the microorganism. Should some, but not all of the detection cells 50 experience a change in light transmitting characteristics, then the total number of the favored microorganism in the specimen can be determined within a range bounded by successive powers of 10, since the total volume of the diluent or water is known and likewise so is the dilution factor.

The detection cells 50 of the cassettes 4 may be observed with the naked eye during incubation, but the electro-optical detector 6 is capable of detecting changes in the light transmitting characteristics with far greater precision and further has the capability of translating the relative optical density of the cells into numbers which may be compared to determine the amount and rate of change in the light transmitting characteristics.

Since the culture medium for each cassette 4 favors a different microorganism, the specimen is analyzed for the number and type of microorganisms corresponding to the number and type of cassettes 4 connected with the manifold 14.

ELECTRO-OPTICAL DETECTOR

Figure 3:
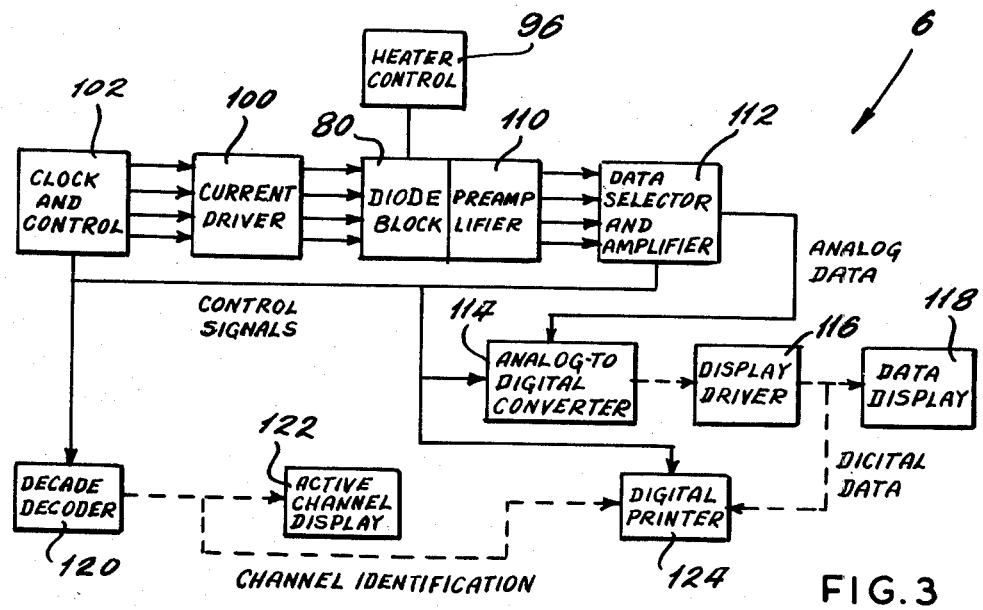
FIG. 3 is a block diagram of the electro-optical detector for measuring the relative optical density of the various cells in the cassette during the incubation of microorganisms therein.
Figure 4:
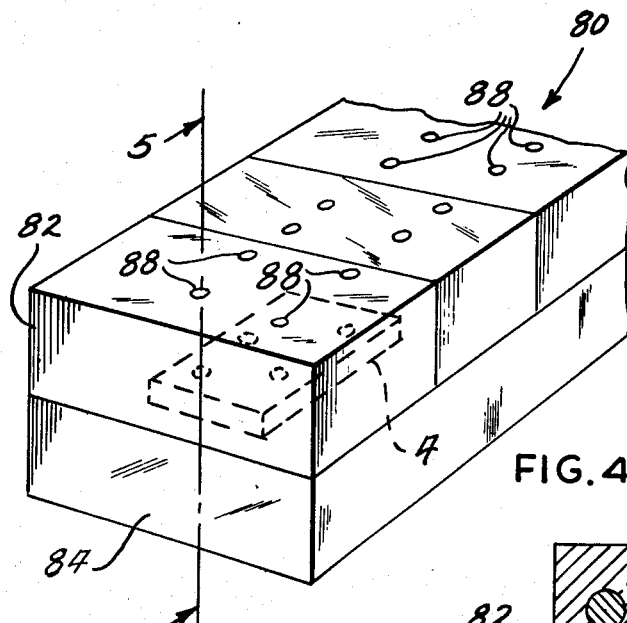
FIG. 4 is a perspective view of the optical detection head forming part of the electro-optical detector.
Figure 5:
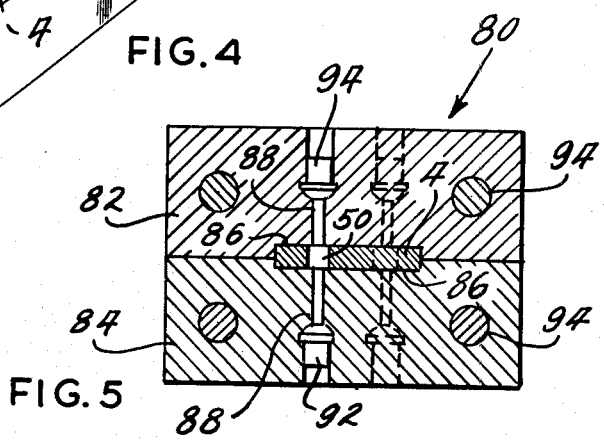
FIG. 5 is a sectional view taken along lines 5—5 of FIG. 4.
Figure 6:
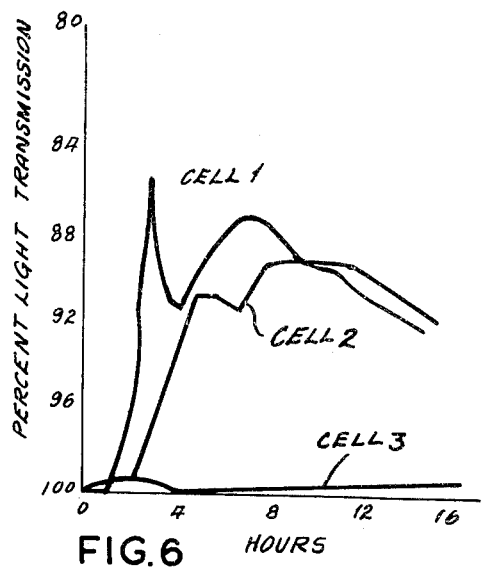
FIGS. 6–13 are typical plots derived from the electro-optical detector.
Figure 8:
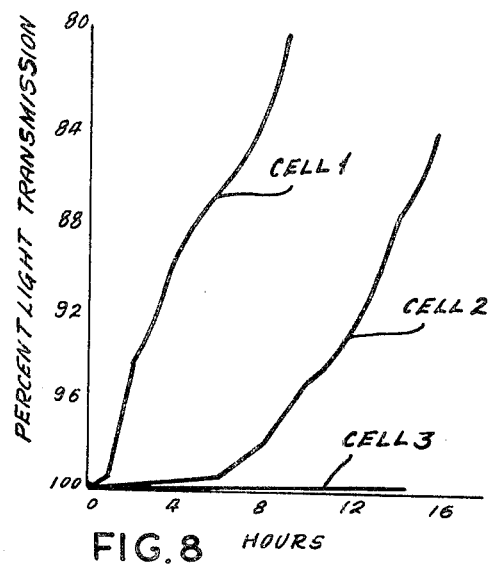
Figure 7:
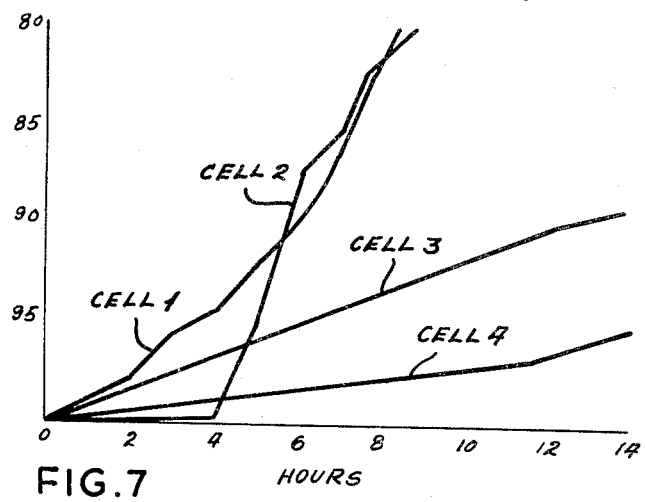
Figure 9:
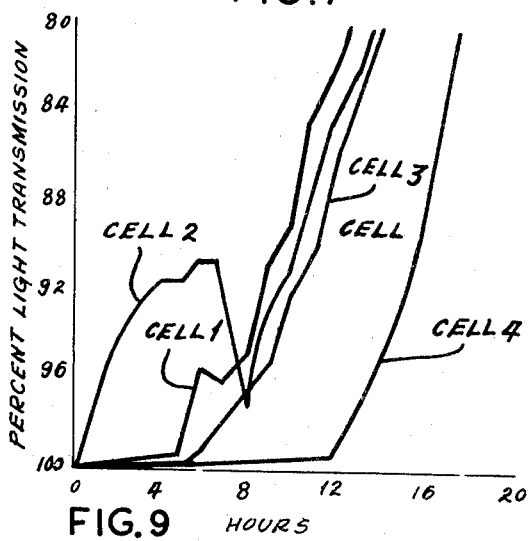

The electro-optical detector (FIG. 3) includes an optical detection head 80 comprising (FIGS. 4 and 5) a pair of aluminum blocks 82 and 84 which fit together and have a multitude of opposed recesses 86 therein. Each pair of opposed recesses 86 is sized to accommodate one cassette 4 and to thereby hold that cassette 4 in a predetermined position between the blocks 82 and 84. For each pair of opposed recesses 86, the blocks 82 and 84 have four sets of aligned bores 88 which open into the recesses 86, and these sets of bores 88 are arranged such that they align with the detection cells 50 in the cassette 4 when the cassette 4 is disposed in those recesses 86. At the outer end of each of its bores 88 the block 82 is fitted solid state emitter diode 90 capable of emitting light at 665 nanometers and projecting that light through its bore 88 as well as through the opposed recesses 86 and the aligned bore 88. Emitters MU 10133 manufactured by the Monsanto Company are ideally suited for this purpose. At the outer ends of each of its bores 88, the other block 84 is provided with a detecting diode 92 which is also of the solid state variety and is capable of detecting the light projected from the corresponding emitter diode 90. When subjected to light from the emitter diode 90, the detecting diode 92 allows a current to flow through it, and the magnitude of that current is proportional to the intensity of light which falls upon the detector diode 90. Thus, the diode 92 is in effect a photocell. A clamping device (not shown) is provided for holding the blocks 82 and 84 together.

Embedded within the blocks 82 and 84 are electric heater elements 94, and these elements derive current through a heater control 96. The heater control 96 maintains the blocks 82 and 84 at 35° C., and accordingly the microorganisms in the cassettes 4 are incubated at that temperature.

The solid state emitter diodes 90 derive current from a current driver 100 having a dedicated channel for each of the diodes 90. The current driver 100 in turn is controlled by a clock and control 102 having a dedicated channel for each of the emitter diodes 90. Among other things, the clock and control 102 causes the current driver 100 to produce a pulsating current which traces as a square wave. As a result each emitter diode 90 projects a pulsating light beam through the detector cell 50 with which it is aligned. Since the beam pulsates, the current flow through opposing detector diode 92 will also pulsate at the same frequency. The clock and control 102 further turns the emitter diodes 90 on and off sequentially, leaving each emitter diode 90 on for two minutes. Thus, eight minutes are required to examine all four detection cells 50 of a single cassette 4.

The detecting diodes 92 detect the pulsating light beams from the emitter diodes 90 aligned with them, and allow a pulsating current to pass through them. The magnitude of this current is proportional to the intensity of the light falling upon them. The diodes 92 are connected with a preamplifier 110 and this preamplifier contains a separate or dedicated preamplifier circuit for each diode 92. These preamplifier circuits amplify the pulsating current signals derived from their respective detecting diodes 92.

The currents derived from the detector diodes 92 and amplified by the separate circuits of the preamplifiers 110 constitute analogue signals. These currents are further amplified in a data selector and amplifier 112 to which the preamplifier 110 is connected. The data selector and control 112 contains a single amplifier and is further connected with and controlled by the clock and control 102. The control provided by the latter component enables the single amplifier of the data selector and amplifier 112 to amplify the individual signals derived sequentially from the separate circuits of the preamplifier 112 so that the output current from the device is delivered through a single channel. This current is likewise an analogue signal.

Connected to the data selector and amplifier 112 and also to the clock and control 102 is an analogue to digital converter 114 which converts the amplified analogue signal derived from the data selector and amplifier 112 into a digital signal. That signal expresses the amplified current from the activated detector diode 92 as a function of time. The converter 114 employs the ramp conversion technique.

The analogue to digital converter 114 is connected with a display driver 116, and the display driver 116 in turn is connected with a data display 118. The former coverts the digital signals into a form compatible with the circuitry of the latter. The display 118 has indicators which numerically display the magnitude of the digital signal in three decimal digits and that corresponds to the magnitude of the analogue signal and to the magnitude of the current flowing through the detector diodes 92. The data display 118 also numerically displays the elapsed time from a selected starting point such as when the incubation in the detection head 80 commenced.

The clock and control 102 is further connected to a decade decoder 120 which in turn is connected to and controls an active channel display 122. The latter indicates which of the emitter diodes 90 is energized and hence which of the cassettes 4 and which detection cell 50 in that cassette 4 has light projecting through it.

Both the display drive 116 and the decade decoder 120 are connected with a digital printer 124 as is the clock and control 102, and this component records the magnitude of the digital signal, the corresponding time at which the signal appeared, and the detecting diode 92 from which the digital signal was derived.

The digital data derived from the digital printer 124 may be plotted on cartesian coordinates (FIG. 6) with the digital signal as the ordinate and the time as the abscissa, in which case there would be four plots for each cassette 4, that is, one for each detection cell 50 therein. (FIGS. 6–13).

In operation, the cassettes 4 after being detached from the manifold 14 are inserted into the optical detection head 80 by placing them in the recesses 86 of blocks 84 and thereafter clamping the blocks 32 over them. The elapsed time between the rehydration of the culture media 66 and the insertion of the cassettes 4 into the optical detection head 80 should not exceed one or two hours, since the microorganisms begin to grow once they are in the solutions containing the culture media. Once all of the cassettes 4 are emplaced in the optical detection head 80, the clock of the clock and control 102 is started and the elapsed time is registered on data display 118. At the same time the clock and control 102 switches the first emitter diode 90 on and this diode projects a beam of light through the first detection cell 50 in the first cassette 4. This beam of light falls on the first detecting diode 92 which allows a current to flow. The magnitude of this current is directly proportional to the intensity of the light leaving the detection cell 50. The dedicated preamplifier 110 for the first detecting diode 92 amplifies this current, and the current is further amplified by the data selector and amplifier 112 which has been switched by the clock and control 102 to conduct only the current from the preamplifier for the first detecting diode 92. The current so amplified constitutes an analogue signal which is delivered to the analogue to digital converter 114, and that component converts the current to a digital signal, which might be considered two signals or currents, one representing the intensity of the light falling upon the first detecting diode 90 and the other representing the time at which the current exists. The display driver 116 converts the digital signal into a format suitable for the data display 118 which shows the elapsed time and the intensity of the light, the latter being in three digits.

The clock and control 102 keeps the first emitter diode 90 on for two minutes, but the data display shows only the intensity of light during the last 45 seconds of that two minute period. The first minute is allowed for transient decay in the data selector and amplifier 112, while during the next 15 seconds the analogue to digital converter 114 resets itself. The final 45 seconds represent the actual reading taken through the first detection cell 50 as previously noted. The channel display 122, which is connected to the clock and control 102 through the decade decoder 120, shows that the reading is derived from the first channel or more particularly from the first detecting diode 92, which corresponds to the first detecting cell 50 in the first cassette 4. The digital printer 124 records the foregoing information, there being one entry for each two minute dwelling on a particular detection cell 50.

After the two minute period for the first detection cell 50, the clock and control 102 turns off the first emitter diode 90 and turns on the second, and the same procedure is repeated for the second detection cell 50. Thus, the intensity of the light passing through the second detection cell 50 is recorded as is the time at which the particular intensity exists. The remaining channels are read in sequence in the same manner.

As the clock and control switches from the fourth channel to the fifth channel, it completes its reading for the first cassette 4 and commences its readings for the second cassette 4, since the fifth through the eighth channels are dedicated to the second cassette 4. Thus, the cassettes 4 are read in sequence as are the individual detection cells 50 within the cassettes 4.

Once the detection cells 50 for all the cassettes 4 have been read, the sequence is repeated. Indeed, the same procedure is carried out at periodic intervals for perhaps 3 to 10 hours and even longer, depending on the nature of the microorganisms the user is looking for. During the entire time the heater elements 94 remain on and keep the cassettes 4 at 35° C.

Initially, the solutions in the various detection cells 50 are clear and hence transmit most of the light projected on them by the emitter diodes 90. The detecting diodes 92 hence receive most of the light emitted from the emitting diodes and this large transmission of light is reflected in the readings appearing on the data display. Thus, low readings on the time display are usually accompanied by high readings on the optical density display. As time passes, the microorganisms grow into cultures or create precipitates in the solutions within the cassettes 4. Hence, the detection cells 50 do not transmit as much light and this is registered in lower readings on the optical density display of the data display 118. Sometimes the optical density for a cell 50 will decrease sharply and then increase for a short period of time before decreasing again. Generally, it takes longer for fungal organisms to effect a change in optical density than bacterial organisms.

In any event, the readings derived from the optical density display and time display of the data display 118 are plotted on cartesian coordinates and usually the readings of four detection cells 50 of a single cassette 4 are plotted on a single graph, thus forming four curves on each graph. The curves for each microorganism are peculiar to that organism or in other words constitute a unique time related signature characteristic for the organism. Thus, if a cassette 44 containing a culture medium 66 which favors a particular microorganism produces plots which correspond to previous plots made for that particular microorganism, then the presence of the microorganism in the specimen is confirmed. On the other hand, if the optical density of the four detection cells 50 for a particular cassette 4 remains unchanged, then the absence of the microorganism which is favored by the culture medium 66 for that cassette is confirmed.

Should the optical density of the solution in some of the detection cells 50 for a particular cassette 4 change but not the remaining, this indicates that an insignificant number of microorganisms exist in the unchanged cells 50. Since the total volume of the water from the reservoir 20 is known, as is the dilution factor through the filters 64 for the cassette 4, the total number of microorganisms in the specimen can be determined, at least between two successive powers of ten.

The following examples are illustrative of readings which may be derived from the electro-optical detector 6 and conclusions which may be drawn from those readings after 16 hours of incubation and analysis.

(1) A cassette (FIG. 4) contained urease medium which favors the proteus microorganism and this cassette was inoculated with human urine by way of the procedure previously described. The cassette 4 was then analyzed in the electro-optical dector 6, and at the end of the analysis the first two detection cells 50 for that cassette 4 have a significant optical density, while the third and fourth cells 50 have no significant changes. The plots derived from the detection cells appear in FIG. 6, and those for the first two cells are similar to previous plots for the proteus microorganism. This confirms that the proteus organism is present. The fact that plots appear in conjunction with only the first and second cells 50 indicates that the total number of the microorganism exceeds $10^2$ but is less than $10^3$.

(2) Another cassette 4 was inoculated with a throat specimen in accordance with the procedure previously described. This cassette 4 contained the medium which favors Staphylococcus. The cassette 4 was thereafter placed in the electro-optical detector 6 and the plot appearing in FIG. 7 resulted. A rapid increase in optical density in the first two cells occurring between the fourth and eighth hour indicates the presence of potentially pathogenic coagulase positive *Staphylococcus aureus*. Non-pathogenic but related organisms normally formed in human throat inocula cause a gradual change in density as seen in cells 3 and 4. It should be noted that the positive reaction observed in cells 1 and 2 further indicates that the inoculum contained more than 1000 organisms of the coagulase positive *S. aureus.*

(3) Still another cassette 4 was inoculated with a throat specimen in accordance with the procedures previously described. This cassette 4 contained the medium which favors Candida. The cassette was thereafter placed in the electro-optical detector 6 and the plot appearing in FIG. 8 resulted. This media has proven so highly selective that only *Candida albicans* has been demonstrated to grow in less than 16 hours. Even closely related Candida species other than *C. albicans* do not yield significant density plots. The degree of separation in the plots between cells 1 and 2 is greatest in slow growing organisms such as fungi (Candida) as compared to rapidly growing bacteria. As in the previous example, the numbers of Candida organisms present in the inoculum can be inferred from the plot.

(4) A cassette 4 containing the medium which favors *Pseudomonas aeruginosa* was inoculated with a urine specimen and was then analyzed with the electro-optical detector 6. The plot appearing in FIG. 9 resulted. The dip in the plots which occurs with certain concentrations of *Pseudomonas aeruginosa* is due to a pigment precursor which is consumed as advanced growth occurs. This is a characteristic signature of *P. aeruginosa* and is seen when density of the growing culture is measured by red light. The hump in the plot is greatest where the concentrations of the organisms is greatest as seen in the cell 1 plot.

(5) Another cassette 4 containing the medium which favors *Escherichia coli* was inoculated with a fecal specimen and then analyzed in the electro-optical detector 6. The plot appearing in FIG. 10 resulted. The plots indicate a rapid light attenuation (increase in density) which is seen only when coliform organisms are present. As in all previous plots, total numbers of coliforms present in the inoculum can be inferred. Growth in cell three after 3 ten-fold dilutions indicates a probability of greater than ten thousand coliform organisms present per ml. of inoculum.

Figure 11:
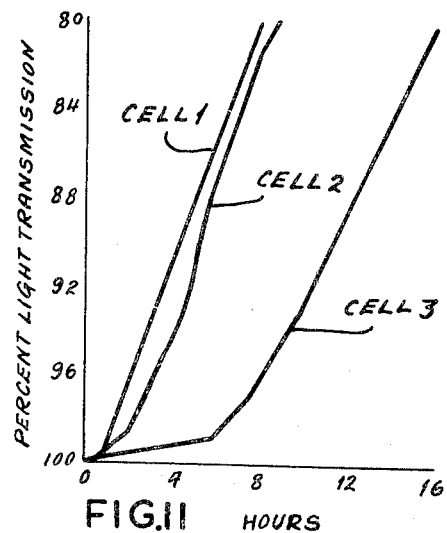
Figure 10:
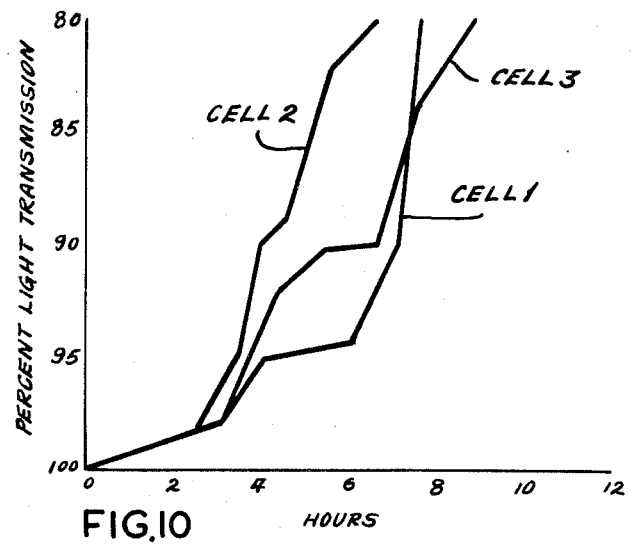
Figure 12:
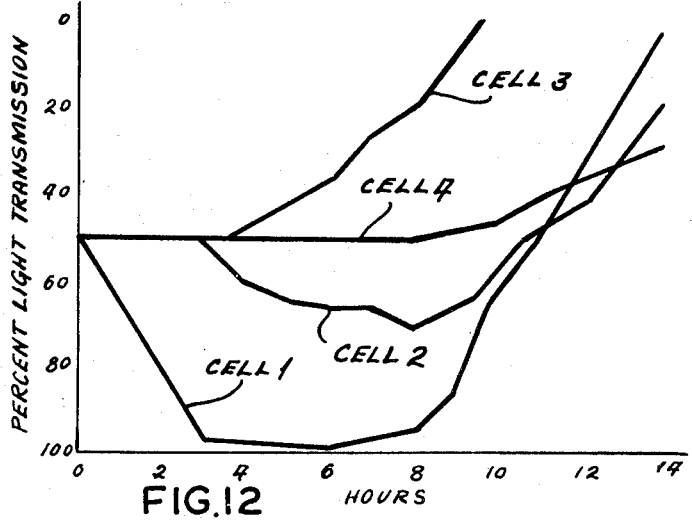
Figure 13:
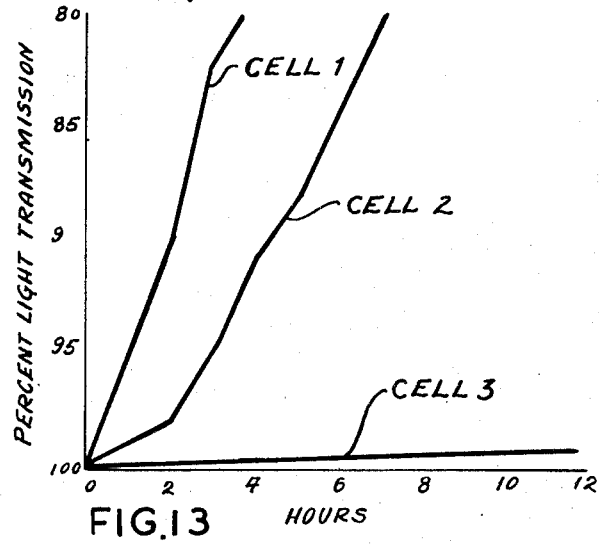

(6) Human urine was introduced into another cassette 4 containing a medium which favors *Salmonella typhosa.* The cassette 4 was then placed in the electro-optical detector 6 and the plot appearing in FIG. 11 resulted. As in most of the previous examples a rapid increase in density signals the presence of one of the pathogenic salmonallae.

(7) Yet another cassette 4 was inoculated with a throat specimen in accordance with the procedures previously described. The cassette contained the medium which favors *Streptococcus pyogenes* (Type A). The cassette 4 was then placed in the electro-optical detector 6 and the plot appearing in FIG. 12 resulted. The plots of the first two cells are characteristic of plots which are seen when beta hemolytic streptococci are present in the inoculum. The dips in the curves which occur in the first few hours of incubation are due to an increase of light transmission which results when the fibrin contained the culture medium is dissolved by the activity of the streptococci. However, sufficient organism multiplication soon decreases the total amount of light and a sharp decrease in light transmission occurs. Inhibitors in the culture medium prevent the growth of organisms capable of dissolving fibrin save the beta hemolytic streptocci. Thus, the characteristic dip in the plot indicates the presence of beta hemolytic streptococci. From the plots in FIG. 12 it is apparent that beta hemolytic streptococci are present in the first two cells and not in cells 3 and 4. Therefore, relative numbers of the streptococci, present in the inoculum can be determined as in the previous examples.

(8) A further cassette 4 was inoculated with a skin specimen in accordance with the procedure previously described. The cassette 4 contained the medium which favors *Herellea vagincola.* The cassette 4 was then placed in the electro-optical detector 6 and the plot appearing in FIG. 13 resulted. The culture medium selects for Herellea while permitting rapid growth and therefore a rapid decrease in light transmission indicates the presence of *Herellea vagincola.*

From the foregoing, it is apparent that specimens are analyzed without engaging in the difficult and time-consuming procedures previously utilized. Moreover, long periods of time are not required for incubating the microorganisms and trial-and-error procedures are eliminated. In addition, the equipment is extremely simple to operate, thus obviating the need for highly skilled personnel. Furthermore, once the bag 18 of the sampling cartridge is sealed, the microorganisms are completely contained and cannot escape, so that the apparatus of the invention is very safe.

This invention is intended to cover all changes and modifications of the example of the invention herein chosen for purposes of the disclosure which do not constitute departures from the spirit and scope of the invention.

What is claimed is:

1. A process for detecting and identifying a specific microorganism in a polymicrobic specimen taken directly from human excretion or secretion without producing cultures, said process comprising diluting the specimen of human excretion or secretion in water; evacuating air from the vicinity of a selective culture medium to create a vacuum in the vicinity of the culture medium, the selective culture medium comprising a source of nutrients favoring growth of a specific microorganism, an inhibitor system for competing microorganisms to avoid false positive responses, and a metabolically responsive indicator which causes the light-transmitting characteristics of the medium to change after dilution of the medium with water as the specific microorganism propagates in the medium; mixing the water-specimen mixture with the selective culture medium after the air is evacuated from the vicinity of the culture medium so as to form a diluent mixture; causing the specific microorganisms to propagate and inhibiting propagation of competing microorganisms; and examining the diluent mixture for a change in the optical characteristics thereof, said change in the optical characteristics indicating the presence of said specific microorganism in said polymicrobic specimen.

2. In combination with a device containing a light-transmitting well, and means for evacuating air from the well of the device to create a vacuum in the well and for thereafter replacing the evacuated air with polymicrobic water specimen, a culture medium located in the well and being capable of sustaining a preselected microorganism to indicate the presence of that microorganism in a polymicrobic water specimen which is introduced into the well by evacuating air from the well with said means and thereafter replacing the evacuated air with the polymicrobic specimen also with said means, the culture medium comprising:

(a) a source of nutrients for enhancing metabolic propagation of at least a single preselected genus of microorganism in polymicrobic specimens in a microenvironment, (b) and a propagation responsive indicator which causes the light-transmitting characteristics of the medium to change after dilution with liquid as the preselected microorganism propagates in said medium, (c) said medium favoring said single preselected microorganism from a specimen containing many organisms.

3. In combination with a cassette including a rigid body having at least one well therein and further having an inlet that opens out of the body and a flow channel leading from the inlet to the well, and means on the body for closing the ends of the well sufficiently to maintain a liquid in the well, said means being transparent to enable light to be projected through the well, whereby a polymicrobic water specimen that is introduced into the cassette at the inlet will flow through the flow channel to the well; a culture medium located in the well and being capable of dispersing in the water specimen when the water specimen enters the well, the culture medium further being capable of sustaining a selected microorganism in the polymicrobic water specimen and indicating the presence of that selected microorganism by reacting with the selected microorganism such that the optical characteristics of the mixture of the water specimen and the culture medium will change in response to the presence of the selected microorganism, but not other microorganisms, whereby the light transmitting characteristics of the well change only when the selected microorganism is in the water specimen.

4. The combination according to claim 3 wherein the body is flat and substantially longer and wider than it is thick so as to have major surface areas and a peripheral edge.

5. The combination according to claim 4 wherein the well extends from one major surface area to the other and the means for closing the ends of the wells is attached to the major surface areas.

6. The combination according to claim 5 wherein the means for closing the ends of the wells comprises transparent tape adhered to the major surface areas of the body and being extended over the ends of the wells.

7. The combination according to claim 4 wherein the inlet opens out of the peripheral edge.

8. The combination according to claim 4 wherein the well is one of a plurality of wells; and wherein the body further contains an overflow channel connected with and extended beyond at least one of the wells.

* * * * *